United States Patent [19]
Davis

[11] Patent Number: 4,570,476
[45] Date of Patent: Feb. 18, 1986

[54] DENSITOMETER PROVING SYSTEM

[75] Inventor: Garland H. Davis, Tulsa, Okla.

[73] Assignee: Santa Fe Pipeline Company, Tulsa, Okla.

[21] Appl. No.: 594,757

[22] Filed: Mar. 29, 1984

[51] Int. Cl.⁴ .................. G01N 9/04; G01D 18/00
[52] U.S. Cl. ...................................... 73/1 R; 73/434
[58] Field of Search .................................. 73/1 R, 434

[56] References Cited

U.S. PATENT DOCUMENTS

| | | | |
|---|---|---|---|
| 2,364,709 | 12/1944 | Greer | 73/1 R |
| 2,745,484 | 5/1956 | Eckstrom et al. | 73/434 X |
| 3,218,841 | 11/1965 | Lerner | 73/1 R |
| 3,812,723 | 5/1974 | Barron | 73/434 |
| 4,195,527 | 4/1980 | Ebeling et al. | 73/434 |
| 4,285,239 | 8/1981 | Heine et al. | 73/434 |

OTHER PUBLICATIONS

"High Vacuum Calibration of a Cyrogenic Quartz Crystal—An Atmospheric Density Gauge"; *The Journal of Vacuum Science and Technology; vol. 8, No. 1; Feb. 1971; pp. 294-298;* Wallace W. Youngblood.

"Installation for Testing Densimeters"; *Meas. Tech. (USA); vol. 21, No. 6, pp. 800-803;* Nov. 1978; M. I. Kondratenko et al.

A Portable Calibration Densimeter for Use in Cyrogenic Liquids"; *Report: NBS Tech. Note 1035;* 16 pages; Mar. 1981; J. D. Siegwarth et al.

*Manual of Petroleum Measurement Standards* Chapter 14–Natural Gas Fluids; Section 6–"Installing and Proving Density Meters Used to Measure Hydrocarbon Liquid with Densities Between 0.3 to 0.7 gm/cc at 15.56° C. (60° F.) and Saturation Vapor Pressure"; Sep. 1979, American Petroleum Institute (API), Title page, pp. i–v, and pp. 1–33.

*Primary Examiner*—Stewart J. Levy
*Assistant Examiner*—Tom Noland
*Attorney, Agent, or Firm*—Willian Brinks Olds Hofer Gilson & Lione Ltd.

[57] ABSTRACT

A trailer mounted densitometer proving system includes three product tanks, each of which stores a respective petroleum product having a differing specific gravity. The product from any one of the three tanks is circulated via an electric pump through a pycnometer, a densitometer being proved, and a heat exchanger. The heat exchanger controls the temperature of the circulating product and a pressure control system controls the pressure of the circulating product. By comparing the pycnometer weight with the densitometer reading, the densitometer can be proved for a wide range of pressures, temperatures and products in order to determine the accuracy of the densitometer under actual working conditions.

15 Claims, 11 Drawing Figures

DENSITOMETER PROVING SYSTEM

BACKGROUND OF THE INVENTION

The present invention relates to an improved system for proving a densitometer, such as a densitometer of the type used in conjunction with pipelines for natural gas liquids.

In pipeline operations the accuracy of densitometers can be critically important. Densitometers are typically used in conjunction with flow meters to measure mass flow into and out of a pipeline, and erroneous densitometer readings can have serious economic consequences. For example, if densities and therefore mass flows into and out of a pipeline are not measured accurately, significant errors resulting in significant losses can result in favor of either a pipeline operator or a pipeline user. For these reasons, a need exists for proving densitometers with high accuracy.

In the past, densitometers have been conventionally proved (i.e., their linearity checked) by calibrating the densitometer with low vapor pressure substances such as air, water, heptane, and the like. In the past, it has often been assumed that if a densitometer is linear for air and water, it is linear for materials with specific gravities between air and water.

SUMMARY OF THE INVENTION

The present invention has resulted from experience that established that the prior art method for proving densitometers was not adequate for pipeline operations such as natural gas liquids pipeline operations. The present invention is directed to an improved densitometer proving system that allows more accurate proving of densitometers under conditions that closely simulate actual densitometer operating conditions.

According to this invention, a densitometer proving system is provided which comprises means for circulating at least one product through a closed circuit. Means are provided for connecting a densitometer and a densitometer calibration device such as a pycnometer to the closed circuit such that the circulating product flows through both the densitometer and the calibration device. Means are also provided for adjustably controlling both the temperature and the pressure of the circulating product in the closed circuit at selected values that can be chosen from predetermined ranges of values characteristic of operating conditions of the densitometer. Finally, means are included for monitoring the densitometer and for displaying information indicative of the density of the circulating product as measured by the densitometer.

In the preferred embodiment discussed below, the densitometer proving system includes at least two product tanks, each of which stores a respective product such as a respective petroleum product. Any selected one of these product tanks can be connected to the closed circuit such that the system can circulate any one of a number of separate products at desired temperatures and pressures through the densitometer in order more completely to simulate operating conditions of the densitometer. In this way, densitometer proving is made more complete and accurate.

The present invention has been found to provide important advantages in actual pipeline operations. In fact, the present invention has been used to demonstrate that certain commercially available densitometers do not meet published specifications of accuracy. Thus, the present invention represents an advance in the art which allows densitometers to be proved more accurately and more thoroughly than before. Mass flow accounting can be performed more accurately, thereby maintaining tighter control over pipeline operations.

The invention itself, together with further objects and attendant advantages, will best be understood by reference to the following detailed description, taken in conjunction with the accompanying drawings.

BRIEF DESCRIPTION OF THE DRAWINGS

FIG. 8b is sectional view taken along 8b—8b of FIG. 8a.

DETAILED DESCRIPTION OF THE PRESENTLY PREFERRED EMBODIMENTS

Figure 1:
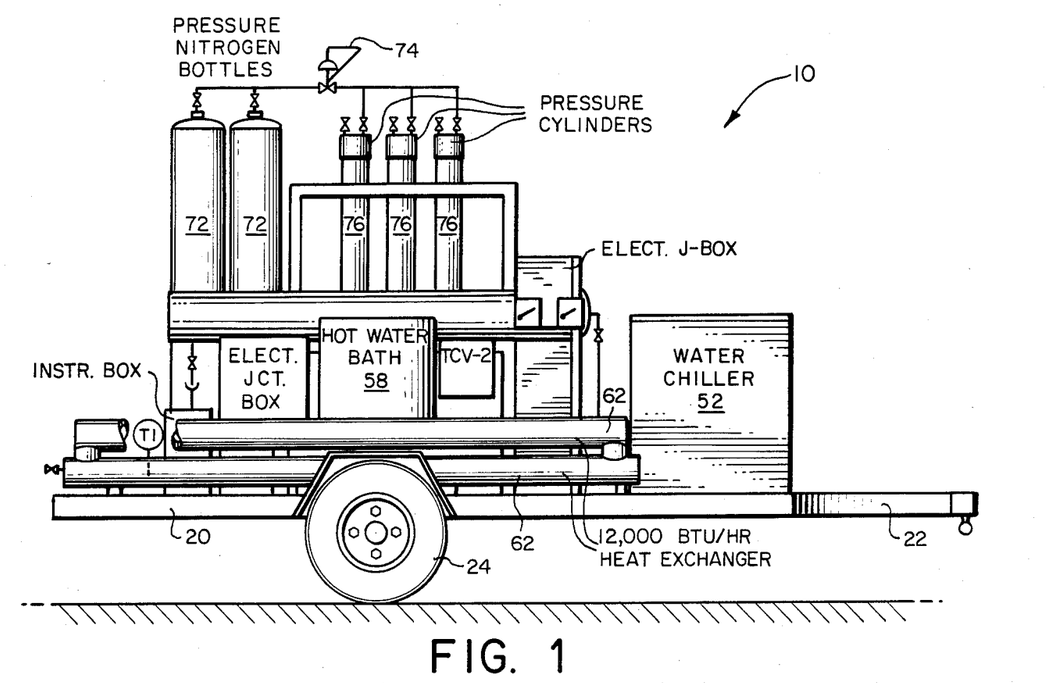
FIG. 1 is a side view of a system which incorporates the presently preferred embodiment of this invention.
Figure 2:
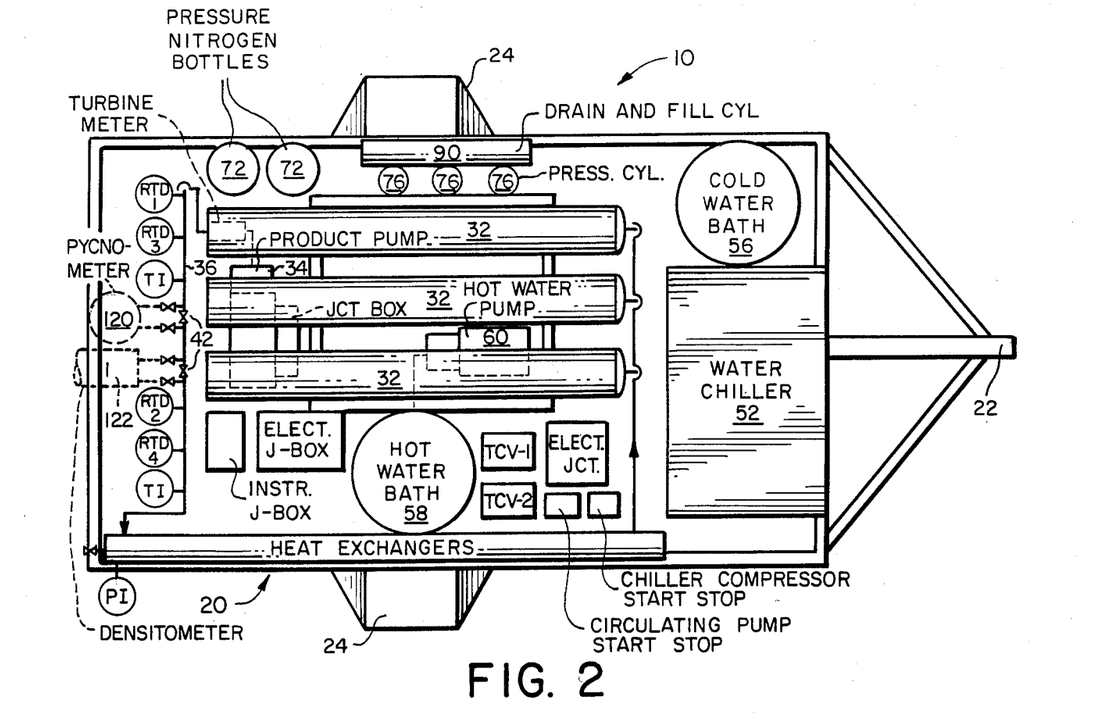
FIG. 2 is a plan view of the system of FIG. 1.

Turning now to the drawings, FIGS. 1 and 2 show a side and plan view, respectively, of a densitometer proving system 10 which embodies the present invention. This densitometer proving system 10 is a self-contained, mobile system mounted on a trailer 20. The trailer 20 includes a trailer hitch 22 and wheels 24. In use, the densitometer proving system 10 can be towed to a densitometer of interest and can be used to prove the densitometer on site. FIGS. 1 and 2 show the general layout of major mechanical components of the system 10.

Figure 3:
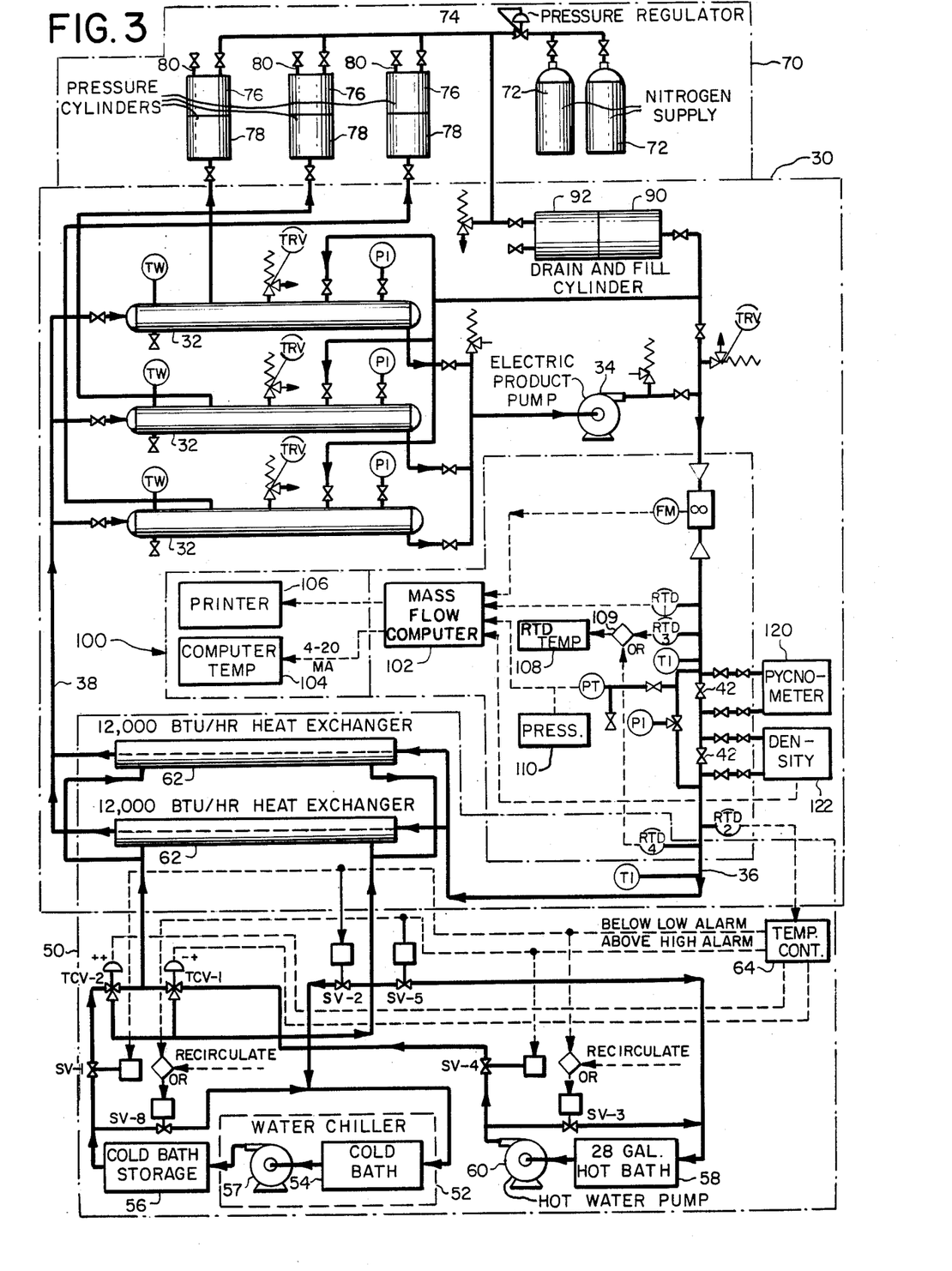
FIG. 3 is a schematic flow diagram of the system of FIG. 1.

FIG. 3 shows a flow diagram of the system 10 of FIGS. 1 and 2. As shown in FIG. 3, this system 10 includes a product circulation system 30. This circulation system 30 in this embodiment includes three product tanks 32. Each of the product tanks 32 contains a respective product to be used in proving a densitometer. Each of the three product tanks 32 is connected via respective valves with a product pump 34. This pump 34 operates to circulate product from one of the product tanks 32 via the conduits 36,38 back to the product tank 32. Thus, when one of the product tanks 32 is connected to the pump 34 and the conduit 38 by the appropriate valves, that product tank 32 cooperates with the pump 34 and the conduits 36,38 to form a closed loop recirculating system in which product from the selected tank 32 is continuously circulated by the product pump 34. As shown in FIG. 3, each of the product tanks 32 includes a respective pressure indicating gauge PI, thermal well TW and thermal relief valve TRV.

The densitometer proving system 10 also includes a temperature control system 50 as shown in FIG. 3. This temperature control system 50 includes a water chiller 52 which includes a first cold water bath 54 and a cold water pump 57. An additional cold water bath 56 is also provided in this embodiment in order to provide a sufficient total volume of about 13 gallons. The water chiller 52 acts as a source of chilled water for cooling the circulating product in the product circulation system 30.

The temperature control system 50 also includes a hot water bath 58 and a hot water pump 60. The hot water bath 58 includes a heater element 59 (FIG. 7c) which operates to heat water in the hot water bath 58.

In addition, two heat exchangers 62 are connected between the conduits 36,38 such that product circulating in the closed loop passes through the parallel heat exchangers 62. In this embodiment, each of the heat exchangers 62 has a capacity of 12,000 BTU's per hour. A temperature controller 64 monitors the temperature of the circulating product in the conduit 36 via a resistance temperature detector RTD-2 and controls the six solenoid valves SV-1 through SV-6 as well as the two temperatures control valves TCV-1,TCV-2 to maintain the temperature of the circulating product at a desired set point. This set point can be manually varied at will in this embodiment at least through the range of 40° L F. to 110° F. For example, if the temperature of the circulating product as measured by RTD-2 is lower than the set point, the temperature controller 64 closes the solenoid valve SV-1 and opens the solenoid valve SV-6 to ensure that the cold water pump 57 recirculates liquid between the two cold water baths 54,56. Simultaneously, the temperature controller 64 closes the solenoid valve SV-3 and opens the solenoid valve SV-4 to allow heated water from the hot water bath 58 to be pumped by the hot water pump 60 to the temperature control valve TCV-1. This temperature control valve TCV-1 is a modulating valve which is controlled by the temperature controller 64 to allow a modulated flow rate of hot water from the hot water bath 58 to flow to the heat exchangers 62. In this example, the temperature controller 64 closes the solenoid valve SV-2 and opens the solenoid valve SV-5 to ensure that return liquid from the heat exchangers 62 passes to the hot water bath 58. In the event the circulating product in the conduit 36 is at a temperature higher than that of the set point, the temperature controller 64 controls the valves to pass chilled water from the cold bath 56 to the heat exchangers 62 and back to the cold bath 54 in order to chill the circulating product. In this way, the temperature of the circulating product in the conduit 36 can be maintained within very close tolerance at a desired set point.

As shown in FIG. 3, the densitometer proving system 10 also includes a pressure control system 70. In this embodiment, the pressure control system 70 includes a pair of nitrogen cylinders 72 which store high pressure nitrogen. These nitrogen cylinders 72 are connected by means of a regulator 74 with three pressure cylinders 76. Each of the pressure cylinders 76 includes a respective piston 78 sliding within it, and each of the pressure cylinders 76 is connected to a respective one of the product tanks 32. Each of the pressure cylinders 76 also includes a respective valved vent line 80.

The pressure control system 70 can be used to control and vary the pressure of the circulating product in the conduits 36,38 within a desired range that extends at least as low as 700 psi and at least as high as 1,400 psi in this embodiment. For example, if the lowermost one of the product tanks 32 is in communication with the conduit 38 and the product pump 34 via the respective valves, the right-handmost pressure cylinder 76 can be used to pressurize the product in that product tank 32 and therefore the circulating product in the conduits 36,38. By varying the set point of the regulator 74, the piston 78 in the pressure cylinder 76 can be moved as necessary to maintain the desired pressure.

The system 10 also includes a drain-fill cylinder 90 which is connected to the conduit 36 near the discharge port of the product pump 34. This drain-fill cylinder 90 includes a sliding piston 92 within it, similar to the piston 78 described above. One end of the cylinder 90 is connected to the regulator 74 by appropriate valves, and the other end of the cylinder 90 is connected both to the three product tanks 32 and to the conduit 36, again by appropriate valves. When it is desired to change the circulating product in the conduits 36,38, the cylinder 90 can be vented and the appropriate valves opened in order to allow product in the conduits 36,38 to flow into the cylinder 90. Once this has been done, the cylinder 90 can be isolated from the conduit 36 by the appropriate valve and then the cylinder 90 can be placed in communication with the appropriate one of the product tanks 32. Once this has been accomplished the regulator 74 can be used to apply pressure to the cylinder 90 in order to move the product in the cylinder 90 into the selected one of the product tanks 32.

Another system included in the densitometer proving system 10 is a measuring system 100 which includes a mass flow computer 102 which is coupled to a computer temperature display 104 and a printer 106. The mass flow computer 102 receives a first input signal from a flow meter FM which in this preferred embodiment is a turbine meter positioned in the conduit 36 to measure the flow rate of product through the conduit 36. The mass flow computer 102 also receives an input signal from the resistance thermal detector RTD-1 indicative of the temperature of the product circulating in the conduit 36. A third input received by the mass flow computer 102 is generated by a pressure transmitter PT and is indicative of the pressure of the product in the conduit 36. This pressure signal is also displayed on a digital pressure display 110. The fourth signal input to the mass flow computer 102 is a signal generated by a densitometer 122 under test. This signal is indicative of the density of the product in the conduit 36 as measured by the densitometer 122. The mass flow computer 102 processes these four inputs to determine and print the density, flow rate and mass flow rate of the product in the conduit 36. Such mass flow computers are well known to those skilled in the art and will not therefore be described in any greater detail here. Purely by way of example and without limitation, the mass flow computer marketed by Elliott Automation of Houston, Tex., as Model No. Micro-2000 has been found to be suitable.

The measuring system 100 also includes a digital temperature display 108 which displays the temperature of product in the conduit 36 as measured either by the detector RTD-3 or the detector RTD-4. A manual switch 109 is used to select which of the two detectors RTD-3 or RTD-4 drives the display 108. The reference symbol TI is used to designate two temperature gauges.

As shown in FIG. 3, the densitometer 122 being proved is connected to the conduit 36 at a position adjacent to that of a pycnometer 120. As is well known to those skilled in the art, a pycnometer is a pressure vessel having a precisely known volume and weight.

Such a pressure vessel can be used to determine the density of a product contained within it. When the valves in the conduit 36 and between the conduit 36 and the pycnometer 120 and the densitometer 122 are positioned properly, the entire flow of product circulating in the conduit 36 flows through the flow meter FM, through the pycnometer 120, and then through the densitometer 122, prior to passing via the conduit 36 to the heat exchangers 62. Of course, in order to obtain this flow path the valves 42 must be closed.

Figure 4:
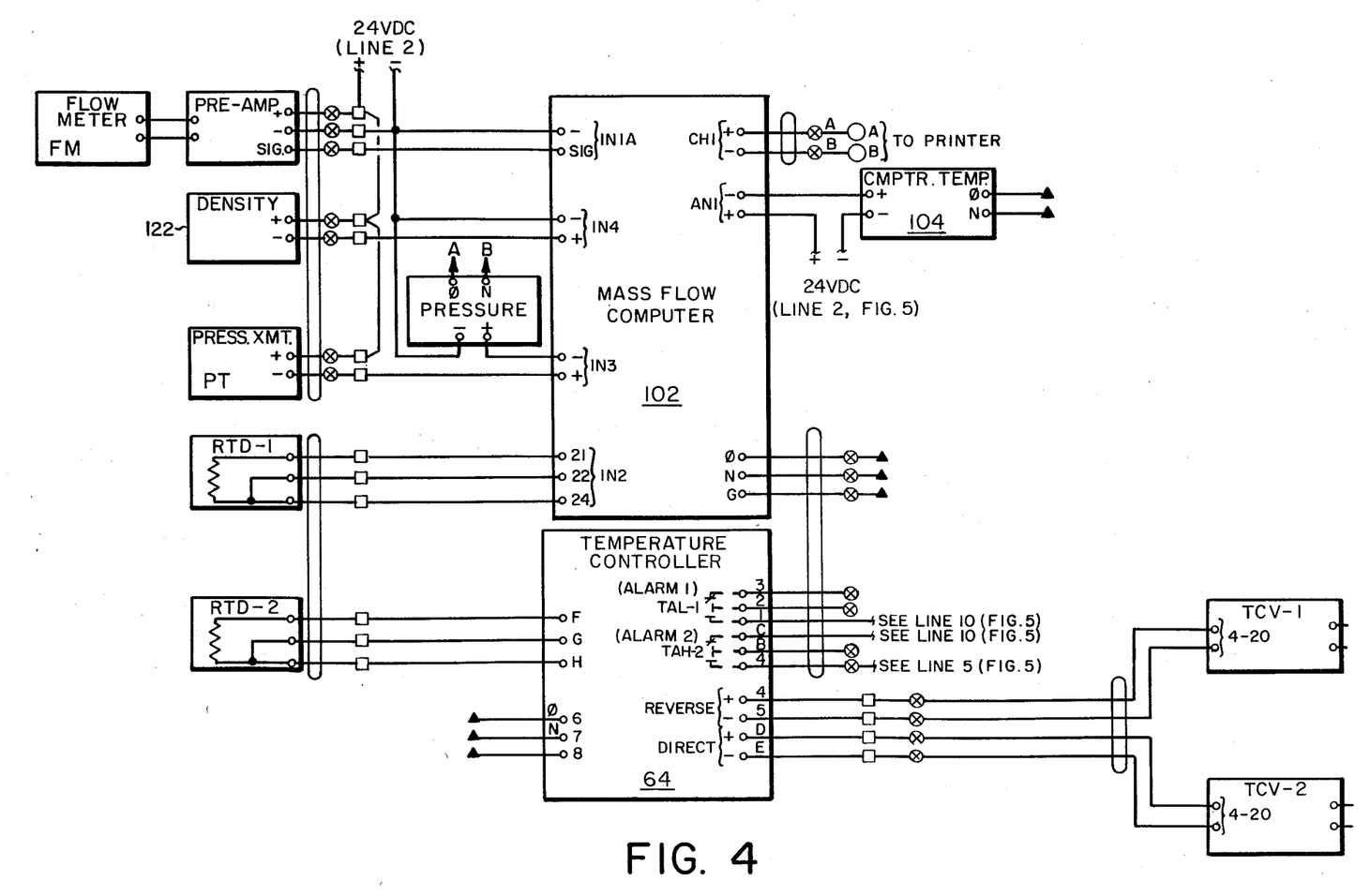
FIG. 4 is an electrical schematic diagram of portions of the system of FIG. 1.

FIG. 4 provides a more detailed electrical schematic diagram showing the electrical connections of the mass flow computer 102 and the temperature controller 64.

Figure 5:
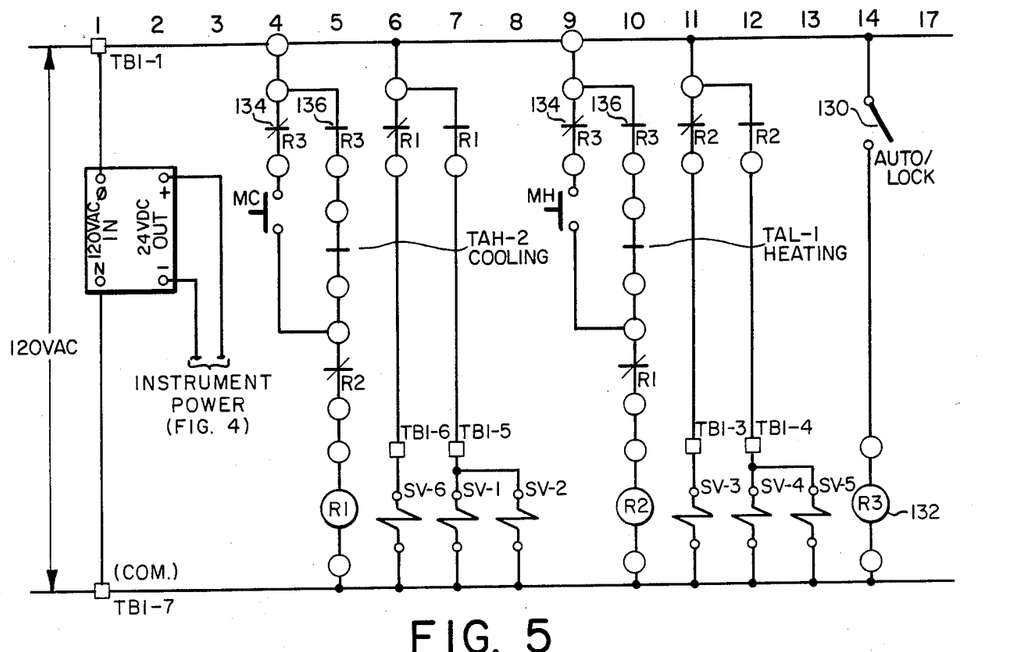
FIG. 5 is an electrical schematic diagram of additional portions of the system of FIG. 1.

FIG. 5 is an electrical schematic diagram showing the manner in which the solenoid valves SV-1 through SV-6 are connected. In FIG. 5 the reference symbol 130 designates a manually controlled auto/local switch. When the switch 130 is closed, the coil 132 of relay R3 is energized. Reference numeral 134 is used to indicate normally closed contacts of the relay R3 which are opened when the coil 132 is energized, and reference numeral 136 is used to indicate normally open contacts of the relay R3 which are closed when the coil 132 is energized. Similar symbols are used for the relay coils of relays R1 and R2 and for the normally open and normally closed contacts of these relays. Reference symbols MC and MH designate manually operated switches for introducing chilled water and heated water, respectively, to the heat exchanger 62 when the system is in the local mode of operation and the switch 130 is open.

Figure 6:
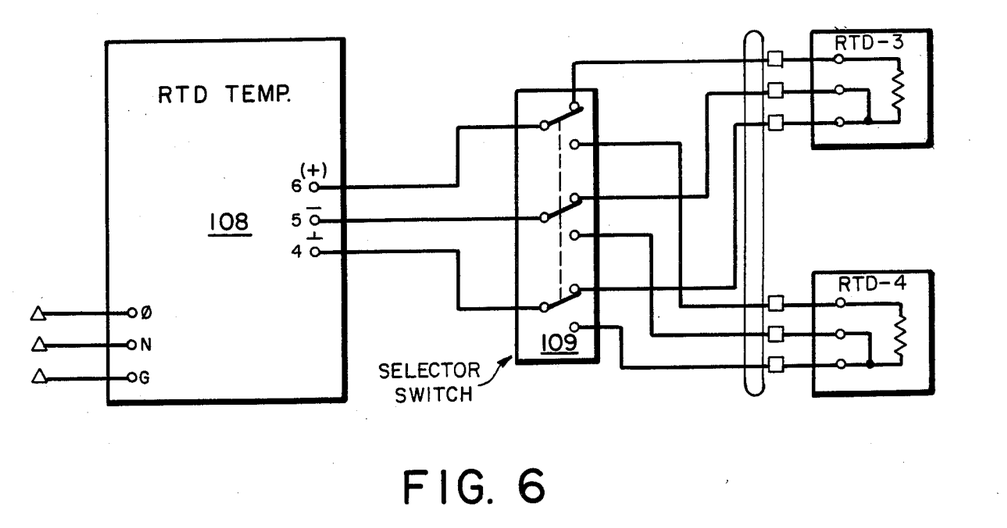
FIG. 6 is an electrical schematic diagram of a temperature monitoring system included in the system of FIG. 1.

FIG. 6 shows a schematic diagram of the manner in which the display 108 is connected by the switch 109 with either selected one of the two sensors RTD-3, RTD-4.

Figure 7A:
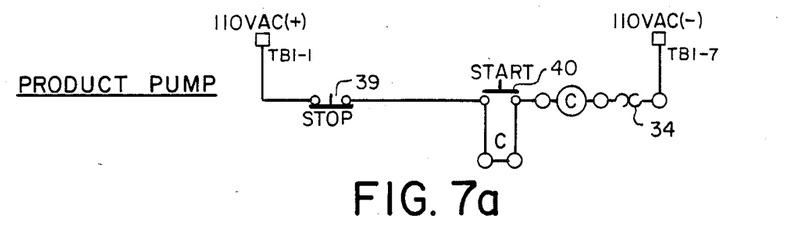
FIGS. 7a, 7b, and 7c are electrical schematic diagrams of control circuitry included in the system of FIG. 1.
Figure 7B:
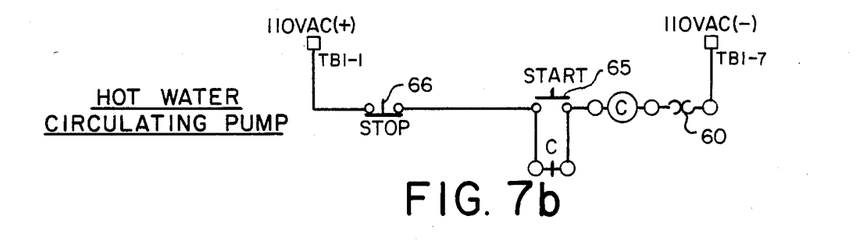
Figure 7C:
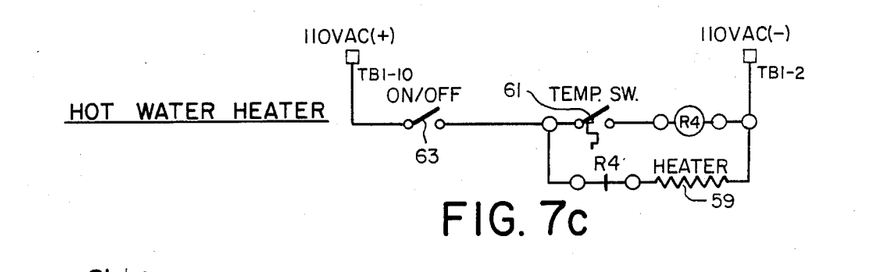

FIGS. 7a–7c show schematic diagrams of the manner in which the product pump 34, the hot water circulating pump 60, and the hot water heater 59 are controlled. In FIG. 7a, the start switch 40 operates to start the product pump 34. Once started, the pump 34 remains in operation by virtue of the action of the relay C until the stop switch 39 is actuated.

Similarly, as shown in FIG. 7b, the hot water circulating pump 60 is activated when the start switch 65 is depressed, and the pump 60 remains activated until the stop switch 66 is depressed.

FIG. 7c shows the manner in which a temperature switch 61 controls a heater 59 included in the hot water bath 58 whenever the on-off switch 63 is closed. In this way, the temperature of water in the hot water bath 58 is automatically maintained at a desired level.

Figure 8A:
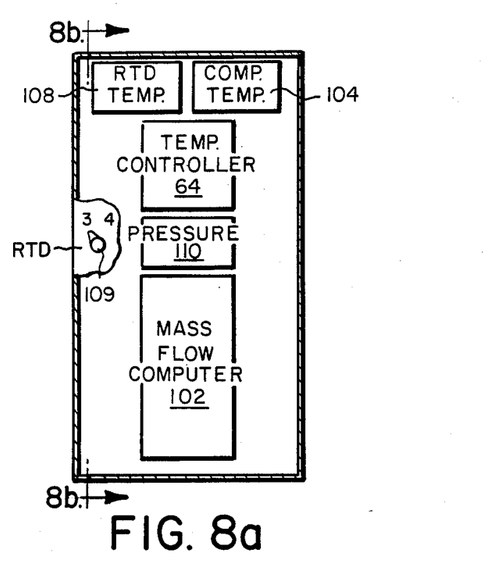
FIG. 8a is a front view of a portable control panel included in the system of FIG. 1.
Figure 8B:
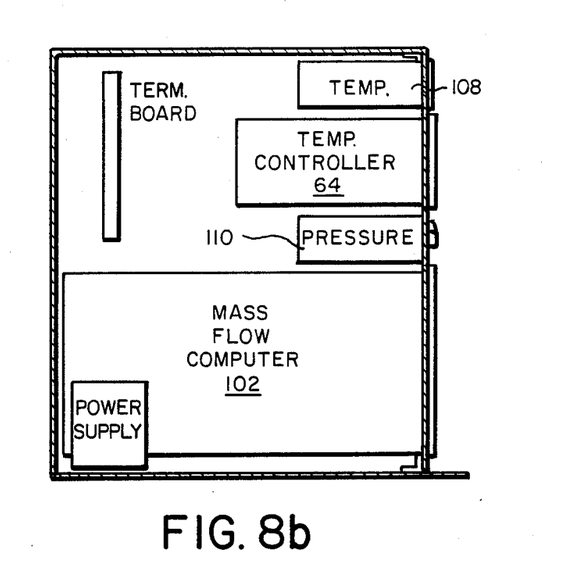

FIG. 8a shows a front view of a portable control panel in which is mounted the mass flow computer 102, the temperature controller 64, as well as the pressure display 110, the computer temperature display 104, and the temperature display 108. This portable control panel is shown in side section in FIG. 8b. The control panel is coupled via 50-foot cable to a junction box included on the trailer 20. This 50-foot cable allows the control panel and the instruments contained within it to be moved away from the trailer and from possibly explosive petroleum vapors.

Purely by way of example and without in any way limiting the scope of this invention, the following information is provided to define additional details of the system 10. In this embodiment, the temperature controller 64 can, for example, be a temperature controller of the type marketed by LFE, Process Control Division of Clinton, Mass., as Model No. 2010, which can control temperature to 0.1° F. The pycnometer 120 can be, for example, a one-liter pycnometer having a volume known to five decimal places, of the type distributed by Arco Anubis of Los Angeles, Calif. A water chiller marketed by Dunham Bush of Marshalltown, Iowa, as Model 45 (modified by well known techniques to be explosion-proof) has been found suitable for use as the water chiller 52, and pump model PL-1E marketed by United Pump Company of Los Angeles, Calif., has been used for the electric product pump 34. In general, any desired temperature sensors, pressure sensors, and flow meters having the desired accuracy of operation can be used. The entire system in this embodiment has been designed to operate at pressures in excess of 1,500 psi, and components have been either selected or modified by well known techniques to operate in an explosion-proof manner. One-half inch valves have been used throughout.

OPERATION

In operation, the densitometer proving system 10 allows the densitometer 122 to be proved under actual operating conditions with high accuracy. In the presently preferred manner of using the system 10, each of the three product tanks 32 is filled with a separate, high vapor pressure petroleum product. In this embodiment, the three petroleum products are (1) modified butane (having a specific gravity of about (0.54), (2) a natural gas mixture such as propane/ethane (having specific gravity of about 0.49), and (3) 80 percent ethane (having a specific gravity of about 0.35–0.39). Preferably, the proving procedures set out at Chapter 14, Section 6 of the *API Measurement Manual* are used.

In order to prove a densitometer 122, a selected one of the product tanks 32 is placed in communication with the conduit 38 and the pump 34 while the remaining two product tanks 32 are isolated from the conduit 38 and the pump 34 by the respective valves. Then the pump 34 is activated by the switch 40 to circulate the selected petroleum product between the conduits 36, 38 via the heat exchangers 62 and the respective selected product tank 32. Then the associated pressure cylinder 76 is used to pressurize the circulating product to the desired pressure by properly adjusting the regulator 74. The temperature controller 64 is then used to adjust the temperature of the circulating product. Once pressure and temperature have stabilized at the desired levels, the valves 42 are checked to ensure that the circulating product passes through both the pycnometer 120 and the densitometer 122. Once the temperature difference between the values measured by RTD-3 and RTD-4 is less than 0.2° F., the mass flow computer 102 is used to measure the density of the circulating product by means of the densitometer 122, and the valves connecting the pycnometer 120 to the conduit 36 are closed to isolate a known volume of the circulating product in the pycnometer 120. The pycnometer 120 is then removed and weighed in order to determine the density of the circulating product. The density as determined by the pycnometer can then be compared with the density as determined by the densitometer 122 in order to determine the accuracy of the densitometer 122. Typically, two pycnometer readings are taken consecutively in order to ensure that the density measured by the pycnometer 120 has been measured properly.

In a typical proving process for a densitometer 122, one of the three available petroleum products such as modified butane will be chosen. Then pressure will be set at a constant value typically greater than 600 psi in order to keep the butane in a liquid state. Generally, in pipelines which are designed to operate with liquid products, it is important to keep the circulating product at a pressure above its vapor pressure to maintain it in a liquid state. After pressure has stabilized, measurements of density with both the pycnometer and the densitometer can then be made at a range of temperatures. Typically, measurements can be made at 20° intervals between 40° F. and 100° F., or even higher if necessary.

After this sequence of temperature variations has been completed, the temperature controller 64 can be used to adjust the temperature of the circulating product to a selected temperature such as 100° F. and then the pressure can be varied. In one preferred embodiment, pressures of 700 psi, 1,100 psi and 1,400 psi are used and the densitometer 122 is proved at each pressure.

After both pressure and temperature variations of the densitometer 122 have been measured with butane, the drain-fill cylinder 90 can be used to remove butane from the conduits 36,38 and return it to the product tank 32 from which it came. Then an entire sequence of pressure and temperature variation measurements can be repeated both with ethane and with the propane/ethane mixture. By varying the product used in the test, the specific gravity of the material measured by the densitometer 122 can be varied.

In the foregoing example of operation of the system 10, the range of temperatures tested was chosen to simulate the actual operating conditions of the densitometer. Similarly, the range of pressures tested simulates the operating range of pressures of the densitometer, and the three products with differing specific gravities were chosen to simulate various materials with which the densitometer 122 is used. By varying temperature, pressure, and product in this manner, the densitometer can be proved throughout its range of operation and its accuracy can be measured under conditions which closely simulate actual operating conditions. Furthermore, calibration factors for the densitometer can be established for each of the test conditions. This complete proving of the densitometer 122 has been found to reveal significant errors of measurement in commercially available densitometers 122, errors which had not previously been detected by commonly used proving methods.

From the foregoing, it should be apparent that an improved densitometer proving system has been described which can be used to prove a densitometer under actual working conditions. In this way, densitometer accuracy can be measured and corrected more accurately, and pipeline operations can be run more efficiently.

Of course, it should be understood that a wide range of changes and modifications can be made to the preferred embodiment described above. For example, the densitometer proving system of this invention can be modified to simulate operating conditions other than those encountered in a natural gas liquids pipeline. Thus, the stored products as well as the temperature and pressure ranges can be varied to suit the actual operating conditions of the densitometer. Furthermore, details of construction can be adapted as needed for particular applications. It is therefore intended that the foregoing detailed description be regarded as illustrative rather than limiting, and that it be understood that it is the following claims, including all equivalents, which are intended to define the scope of this invention.

I claim:

1. A densitometer proving system comprising:
    means for repeatedly recirculating at least one high vapor pressure product through a closed circuit;
    means for connecting a densitometer calibration device to the closed circuit such that said at least one product flows through the calibration device;
    means for connecting a densitometer to the closed circuit such that said at least one product flows through the densitometer, said densitometer operative to generate a signal indicative of the density of the at least one product;
    means for adjustably controlling the temperature of said at least one product in the closed circuit at a selected temperature chosen from a predetermined range of temperatures;
    means for adjustably controlling the pressure of said at least one product in the closed circuit at a selected pressure chosen from a predetermined range of pressures; and
    means, responsive to the signal, for displaying information indicative of the density of the at least one product measured by the densitometer.

2. The invention of claim 1 wherein the circulating means comprises:
    at least two product tanks, each storing a respective product;
    means for connecting either selected one of the two product tanks to the closed circuit; and
    a pump, included in the closed circuit, for circulating the product from a connected one of the product tanks through the closed circuit.

3. The invention of claim 2 wherein the product in a first of the at least two product tanks is a petroleum product with a specific gravity less than about 0.4, and wherein the product in a second of the at least two product tanks is a petroleum product with a specific gravity greater than about 0.5

4. The invention of claim 3 wherein the at least two product tanks further comprise a third product tank which stores a petroleum product having a specific gravity greater than that of the petroleum product in the first product tank and less than that of the petroleum product in the second product tank.

5. The invention of claim 1 wherein the temperature controlling means comprises:
    a heat exchanger in thermal contact with the closed circuit;
    a source of chilled fluid;
    a source of heated fluid;
    means for selectively interconnecting the heat exchanger with the sources of heated and chilled fluid; and
    control means for controlling the interconnecting means to maintain said at least one product at the selected temperature.

6. The invention of claim 5 wherein the predetermined range of temperatures extends at least between about 40° F. and about 100° F.

7. The invention of claim 1 wherein the pressure controlling means comprises:
    a source of compressed gas;
    means for connecting the gas source to the closed circuit; and means for regulating the pressure of the compressed gas applied to the closed circuit in order to regulate the pressure of the product in the closed circuit.

8. The invention of claim 7 wherein the predetermined range of pressures extends at least between about 700 psi and about 1400 psi.

9. A self-contained, mobile densitometer proving system comprising:
a mobile platform;
at least two product tanks mounted on the platform, each storing a respective petroleum product having specific gravities which differ from one another;
a heat exchanger mounted on the platform;
means for circulating the petroleum product from any selected one of the product tanks through the heat exchanger in a closed circuit;
means, mounted on the platform, for selectively supplying heat to and removing heat from the heat exchanger as necessary to maintain the circulating petroleum product at a selected temperature chosen from a predetermined temperature range;
means, mounted on the platform, for selectively pressurizing the circulating petroleum product to maintain the circulating petroleum product at a selected pressure chosen from a predetermined pressure range;
means for connecting a densitometer calibration device to the closed circuit such that the circulating petroleum product flows through the calibration device;
means for connecting a densitometer to the closed circuit such that the circulating petroleum product flows through the densitometer, said densitometer operative to generate a signal indicative of the density of the at least one petroleum product; and
means, responsive to the signal, for displaying information indicative of the density of the circulating petroleum product measured by the densitometer.

10. The invention of claim 9 wherein the petroleum product in a first of the at least two product tanks has a specific gravity less than about 0.4, and wherein the petroleum product in a second of the at least two product tanks has a specific gravity greater than about 0.5.

11. The invention of claim 10 wherein the at least two product tanks further comprise a third product tank storing a petroleum product having a specific gravity greater than that of the petroleum product of the first product tank and less than the petroleum product of the second product tank.

12. The invention of claim 9 wherein the predetermined temperature range extends at least as low as 40° F. and at least as high as 100° F.

13. The invention of claim 9 wherein the predetermined pressure range extends at least as low as 700 psi and at least as high as 1400 psi.

14. A self-contained, mobile densitometer prover comprising:
a trailer;
three product tanks mounted on the trailer, each storing a respective petroleum product having a density of less than 0.40, between 0.40 and 0.50, and greater than 0.50, respectively;
a heat exchanger mounted on the trailer;
a pump;
first means for connecting the three product tanks to the pump;
second means for connecting the pump to the heat exchanger;
third means for connecting the heat exchanger to the three product tanks, said first, second and third means cooperating with the pump and the heat exchanger to circulate the petroleum products from the product tanks in a closed loop;
valve means for isolating selected ones of the product tanks from the closed loop;
a source of heated liquid, said source mounted on the trailer;
a source of chilled liquid, said source mounted to the trailer;
means for controlling the flow of heated and chilled liquid to the heat exchanger to maintain the temperature of the circulating petroleum product at a temperature selectable from the range of 40° F.–100° F.;
a source of pressurized gas;
means for coupling the pressurized gas to the closed loop to pressurize the circulating petroleum product;
regulator means for regulating the pressure of the pressurized gas coupled to the closed loop to a pressure selectable from the range of 700 psi–1400 psi;
means for connecting a pycnometer to the closed loop such that the circulating petroleum product circulates through the pycnometer;
means for connecting a densitometer to the closed loop adjacent to the pycnometer such that the circulating petroleum product circulates through the densitometer; and
a mass flow computer coupled to the densitometer to display the density of the circulating petroleum product as measured by the densitometer.

15. The invention of claim 14 further comprising:
a drain-fill tank which comprises a sliding piston within the drain-fill tank, said drain-fill tank defining a first end coupled to the source of pressurized gas and to a valved vent, and a second end coupled to each of the three product tanks and to the second means.

* * * * *